United States Patent [19]

Kung et al.

[11] Patent Number: 5,334,728

[45] Date of Patent: Aug. 2, 1994

[54] DOPAMINE RECEPTOR LIGANDS AND IMAGING AGENTS

[75] Inventors: Hank F. Kung, Wynnewood; Raymond Murphy, Philadelphia, both of Pa.

[73] Assignee: The Trustees of The University of Pennsylvania, Philadelphia, Pa.

[21] Appl. No.: 957,259

[22] Filed: Oct. 6, 1992

Related U.S. Application Data

[62] Division of Ser. No. 816,140, Dec. 31, 1991, Pat. No. 5,186,921, which is a division of Ser. No. 339,006, Apr. 17, 1989, Pat. No. 5,122,361.

[51] Int. Cl.$^5$ .............. C07F 7/22; C07F 7/10; C07F 3/14; C07D 403/12
[52] U.S. Cl. ...................... 548/402; 548/406
[58] Field of Search ............... 548/402, 406

[56] References Cited

U.S. PATENT DOCUMENTS

| | | | |
|---|---|---|---|
| 4,656,280 | 4/1987 | Garlick | 546/20 |
| 4,739,060 | 4/1988 | Saji et al. | 546/20 |
| 4,888,353 | 12/1989 | Lednicer et al. | 514/422 |
| 5,006,570 | 4/1991 | Franceschini | 514/422 |

OTHER PUBLICATIONS

Translation of Claim 1 of JP Kokai 58-62554 (1984).
Kung et al., *Journal of Medicinal Chemistry*, 331, 171–178, 1990.
Ogren, S. O. et al., *European Journal of Pharmacology* 102, 459–474, 1984.
Florvall, L. et al., *J. Med. Chem.* 25, 1280–1286, 1982.
De Paulis, T. et al., *J. Med. Chem.* 28, 1263–1269, 1985.
Hogberg, T. et al., *Acta Pharm. Suec.* 2424, 289–328, 1987.
Kohler, C. et al., *Biochemical Pharmacology* vol. 34 No. 13, 2251–2259, 1985.
Janowsky, A. et al., *European Journal of Pharmacology* 150, 203–205, 1988.
Kung, H. F. et al., *Journal of Medicinal Chemistry* 31, 1039, 1988.
Kung, H. F. et al., *Nucl. Med. Biol.* vol. 15 No. 2, 195–201, 1988.
Halldin, C. et al., *Journal of Labelled Compounds and Radiopharmaceuticals* vol. XXIII, Nos. 10–12, 1405–1406 (1986).
Farde, L. et al., *Arch Gen. Psychiat.* 44, 671, 1987.
Farde, L. et al., *Psychopharmacology* 94, 471–478, 1988.
European Patent Application Publication No. 147,044, published on Jul. 3, 1985.
U.K. Patent Application GB 2176785A, published on Jan. 7, 1987.
European Patent Application 207,913, published Jan. 7, 1987.
European Patent Application 234,872, published Sep. 2, 1987.
Kung, H. F. et al., *Journal of Nuclear Medicine* 30, 88, 1989.
Adam, M. J. et al., *Int. J. Appl. Radiat. Isot.* vol. 36 No. 12 935–937, 1985.
De Paulis Chemical Abstracts vol. 109, No. 15, Oct. 10, 1988 p. 665, column 2, Ref. No. 128757P.
Murphy et al. Chemical Abstracts, vol. 112, No. 5, Jan. 29, 1990, p. 555, column 2, Ref. No. 35611H.

*Primary Examiner*—Mark L. Berch
*Attorney, Agent, or Firm*—Woodcock Washburn Kurtz Mackiewicz & Norris

[57] ABSTRACT

Novel CNS dopamine D-2 receptors, such as the compound 5-iodo-7-N-[(1-ethyl-2-pyrrolidinyl)methyl]carboxamide-2,3-dihydrobenzofuran, are disclosed. These compounds are useful as imaging agents for D-2 receptors in the human brain and exhibit good brain retention and in vivo stability.

12 Claims, 1 Drawing Sheet

DOPAMINE RECEPTOR LIGANDS AND IMAGING AGENTS

This is a division, of application Ser. No. 816,140, filed Dec. 31, 1991 U.S. Pat. No. 5,186,921 which is a division of Ser. No. 339,006 filed Apr. 17, 1989 now U.S. Pat. No. 5,122,361 issued Jun. 16, 1992.

BACKGROUND OF THE INVENTION

This invention relates to benzamine derivatives which are selective for dopamine D-2 receptors, to methods of preparing such compounds, to methods of utilizing them as imaging agents, and to novel compounds useful as intermediates in the preparation of such D-2 receptors.

Dopamine is a neural transmitter, a chemical that is used to send messages from one brain cell to another. Neurotransmitters bind to special receptor proteins in the membrane of nerve cells, like a key in a lock, triggering a chemical reaction within the cell. Imbalances in dopamine production and use have been implicated in a variety of mental disorders. Insufficient production of dopamine, for example, causes Parkinson's disease which affects more than a million people in the United States. Its symptoms include tremors and rigidity of limbs, and treatment involves replacing the dopamine through drugs or by implanting dopamine-secreting tissues into the brain. An excess production of dopamine, in contrast, is thought to be one of the major factors in the development of schizophrenia, which is characterized by disordered thought, hallucinations and inappropriate emotional responses. An estimated three million people in the United States suffer from schizophrenia, including forty percent of all patients in mental hospitals. Anti-psychotic drugs such as chlorpromazine and haloperidol, which halt hallucinations and delusions, are used to treat schizophrenia because they bind to the D-2 dopamine receptors, preventing the excess dopamine from overstimulating them.

For the treatment of a wide variety of different nervous and mental diseases such as schizophrenia and Parkinson's Disease, it is desirable to be able to monitor the effectiveness of drugs and substances which affect brain chemistry. For instance, it is highly desirable to be able to gauge the biochemical effects of drugs administered for blocking the patient's dopamine receptors. If too little of the drug is administered, the desired blockade does not occur, and if too much of the drug is administered, there can be severe side effects.

New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs is based upon the comparisons made.

It is generally accepted that there are two subtypes of dopamine receptors, designated as D-1 and D-2 receptors. Recent reports have suggested that these two subtypes of receptors exhibit opposite biochemical effects: D-1 agonists stimulate adenyl cyclase activity, while D-2 agonists inhibit the enzyme activity. It is clear that these receptor subtypes influence each other, and yet they display separate and distinct functions on body physiology and biochemistry. Monitoring of D-2 receptors in a patient is important for assessing the dopaminergic system and ultimately assisting patient management.

A variety of substituted benzamide derivatives possessing antipsychotic and antiemetic properties have been reported. (Ogren, S. O., Hall, H., Kohler, C., et al. Eur. J. Pharmacol. 1984, 102,459; Florvall, L., Ogren, S. J. Med. Chem. 1982, 25, 1280; de Paulis, T., Kumar, Y., Johansson, L., et al. J. Med. Chem. 1985, 28, 1263; Hall, H., Wedel, I. Acta Pharmacol. Toxicol. 1986, 58, 363; Hogberg, T., Ramsby, S., Ogren, S., Norinder, U. Acta Pharm. Suec. 1987, 24, 289). The pharmacological effects of these agents are assumed to be induced by blocking the CNS D-2 dopamine receptor. In this series of benzamide derivatives, agents with an N-ethyl-pyrrolidinyl-methyl amine group appear to be the most attractive antagonists, showing the best selectivity and the highest affinity for the CNS D-2 dopamine receptor. Raclopride (Kohler, C., Ogren, S., Gawell, L. Biochem. Pharmacol. 1985, 34, 2251) and eticlopride (Kohler, C., Hall, H., Gawell, L. Eur. J. Pharmacol. 1986, 120, 217; Hakan, H., Kohler, C., Gawell, L. Eur. J. Pharmacol. 1985, 111, 191) are two excellent examples which show specific D-2 antagonistic activity, with high affinity in rat striatum tissue preparations and low nonspecific binding. See Table 1. Radioactive benzamides are not only potentially useful as imaging agents (labeled with $^{123}$I, $T_{\frac{1}{2}}=13$ h, gamma ray energy=159 keV), but are also very valuable as pharmacological tools for probing the D-2 dopamine receptor under in vitro and in vivo conditions (labeled with $^{125}$I, $T_{\frac{1}{2}}=60$ d, gamma energy=30–65 keV). Several iodinated benzamide derivatives, iodosulpiride (Martres, M.-P., Sales, N., Bouthenet, M.-L., Schwartz, J.-C. Eur. J. Pharmacol. 1985, 118, 211), iodoazidoclebopride (Neumeyer, J. L., Guan, J.-H., Niznik, H. B., Dumbrille-Ross, A., Seeman, P., Padmanabhan, S., Elmaleh, D. R. J. Med. Chem. 1985, 28, 405), iodopride (Janowsky, A., de Paulis, T., Clanton, J. A., Smith, H. E., Ebert, M. H., Kessler, R. M. Eur. J. Pharmacol. 1988, 150, 203) and IBZM (Kung, H. F., Billings, J. J., Guo, Y.-Z., Xu, X., Mach, R. H., Blau, M., Ackerhalt, R. A. Nucl. Med. Biol. 1988, 15, 195; Kung, H. F., Billings, J. J., Guo, Y.-Z., Mach, R. H. Nucl. Med. Biol. 1988, 15, 203; Kung, H. F., Kasliwal, R., Pan, S., Kung, M.-P., Mach, R. H., Guo, Y.-Z. J. Med. Chem. 1988, 31, 1039) have been reported as showing very high affinity and selectivity to the D-2 dopamine receptor in the same striatal membrane preparation.

TABLE 1
Chemical Structures and In Vitro Binding Constants of Benzamides

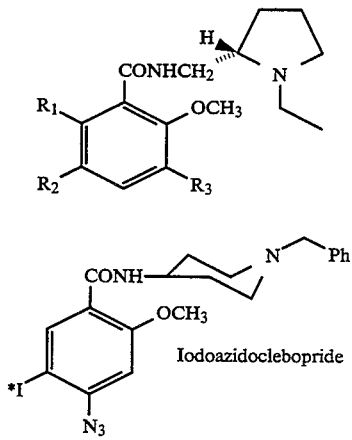

| Compound | R$_1$ | R$_2$ | R$_3$ | K$_d$ (nM) |
|---|---|---|---|---|
| Iodosulpiride | H | SO$_2$NH$_2$ | H | 1.5 |
| Raclopride | OH | Cl | Cl | 1.1 |
| Eticlopride | OH | C$_2$H$_5$ | Cl | 0.17 |
| IBZM | OH | I | H | 0.43 |
| BZM | OH | H | H | 31.1 |
| Iodopride | H | I | H | 3.0* |
| Iodoazidoclebopride | — | — | — | 14 |

*IC$_{50}$ against [H$^3$]spiperone binding of rat striatal tissue preparation.

Imaging studies of CNS D-2 dopamine receptor in humans with [$^{11}$C]raclopride (labeled at the N-ethyl group), in conjunction with positron emission tomography (PET), have been reported. (Farde, L., Ehrin, E., Eriksson, L., et al. Proc. Natl. Acad. Sci. (USA) 1985, 82, 3863; Haldin, C., Stone-Elander, S., Farde, L., et al. J. Labeled Compd. Radiopharm. 1986, 23, 1408; Ehrin, E., Farde, L., de Paulis, T., et al. Int. J. Appl. Rad. Isot. 1985, 36, 269; Farde, L., Hall, H., Ehrin, E., et al. Science 1986, 231, 258; Farde, L., Hall, H., Pauli, S., et al. Psychopharmacol. 1988, 94, 471; Farde, L., Wiessel, F. A., Hall, H., Halldin, C., Stone-Elander, S., Sedvall, G. Arch. Gen. Psychiat. 1987, 44, 671). A high ratio of specific striatal to nonspecific cerebellar binding in living human brain was observed. Using an equilibrium model and Scatchard plots, the affinity constant (K$_d$=7.1 nM, B$_{max}$=15 pmole/ml) in living human brain was measured by PET. (Farde, L., Hall, H., Pauli, S., et al. Psychopharmacol. 1988, 94,471; Farde, L., Wiesel, F. A., Hall, H., Halldin, C., Stone-Elander, S., Sedvall, G. Arch. Gen. Psychiat. 1987, 44, 67 1 ). The values for the dopamine D-2 receptor density were comparable to those determined earlier using a different imaging agent, N-methylspiperone (K$_d$=0.097 nM, B$_{max}$=16.6 pmole/g). (Wagner, H. N., Burns, H. D., Dannals, R. J., et al. Science 1983, 221, 1264; Wong, D. F., Wagner, H. N., Dannals, R. J., et al. Science 1984, 226, 1393; Wong, D., Gjedde, A., Wagner, H. N. J. Cereb. Blood. Flow. Metab. 1986, 6, 137). Planar imaging studies in humans with S-[$^{123}$I]IBZM (S—the active isomer, R—the inactive isomer), immediately after intravenous injection, demonstrate that this agent, as expected, displayed high concentration in basal ganglia of the brain. Single photon emission computed tomography (SPECT) imaging of normal human brain at 1 hour postinjection displayed a pattern which clearly indicates the highly specific uptake in the basal ganglia of the brain. (Kung, H. F., unpublished data).

Several other potential SPECT and PET dopamine receptor imaging agents, based on radiolabeled spirperone or its derivatives, have been reported. (Saji, H., Nakatzuka, I., Shiba, K. Life Sci. 1987, 41, 1999; Nakatzuka, I., Saji, H., Shiba, K., et al. Life Sci. 1987, 41, 1989; Shine, C.-Y., Bai, L.-Q., Teng, R.-T., et al. J. Nucl. Med. 1987, 28, 1164; Chi, D. Y., Kilbourn, M. R., Katzenellenbogen, J. A., et al. Appl. Radiat. Isot. 1986, 12, 1173; Kiesewetter, D. O., Eckelman, W. C., Cohen, R. W., et al. Appl. Radiat. Isot. 1986, 12, 1181; Welch, M. J., Chi, D., Mathias, C. J., et al. Nucl. Med. Biol. 1986, 12, 523; Satyamurthy, N., Bida, G. T., Barrio, J. R., et al. Nucl. Med. Biol. 1986, 13,617; Coenen, H. H., Laufer, P., Stoecklin, G., et al. Life Sci. 1987, 40(1), 81; Arnett, C. D., Fowler, J. S., Wolf, A. P. Life Sci. 1985, 36, 1359; Owen, F., Crawley, J., Cross, M., et al. Br. Pshychopharm. Monogr. 1985, 216, 227; Crawley, J. C. W., Crow, T. J., Johnstone, E. C., et al. Nucl. Med. Comm. 1986, 7, 599). Preliminary studies of an iodinated 2'-iodo-spiperone (2'-ISP) indicate that the spiperone analog displays excellent D-2 specificity (Kd=0.25 nM, rat striatum) and in vivo stability as compared to the 4-iodo-spiperone (Gundlach, A. L., Largent, B. L., Synder, S. H. Life Sci. 1984, 35, 1981) reported earlier. In vitro binding data for 2'-ISP appears to show a higher nonspecific binding (40%) than that observed with [$^{125}$I]IBZM (5%). (Kung, H. F., Kasliwal, R., Pan, S., Kung, M.-P., Mach, R. H., Guo, Y.-Z. J. Med. Chem. 1988, 31, 1039). In addition, several new $^{18}$F labeled compounds including spiperone itself, N-methyl spiperone (Arnett, C. D., Fowler, J. S., Wolf, A. P. Life Sci. 1985, 36, 1359), N-fluoroalkyl-spiperones (Welch, M. J., Chi, D., Mathias, C. J., et al. Nucl. Med. Biol. 1986, 12, 523; Satyamurthy, N., Bida, G. T., Barrio, J. R., et al. Nucl. Med. Biol. 1986, 13, 617; Coenen, H. H., Laufer, P., Stoecklin, G., et al. Life Sci. 1987, 40(1), 81; Arnett, C. D., Fowler, J. S., Wolf, A. P. Life Sci. 1985, 36, 1359) and [$^{77}$Br]4-bromospiperone have been reported. (Owen, F., Crawley, J., Cross, M., et al. Br. Pshychopharm. Monogr. 1985, 216, 227; Crawley, J. C. W., Crow, T. J., Johnstone, E. C., et al. Nucl. Med. Comm. 1986, 7, 599). The structures of several of the above-mentioned compounds are illustrated in Table 2.

TABLE 2
Chemical Structures of Spiperone-Based Dopamine Receptors

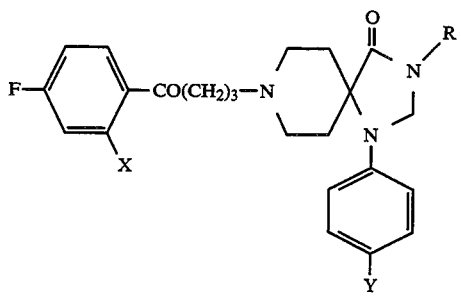

| Compound | R | X | Y |
|---|---|---|---|
| Spiperone | H | H | H |
| N-methyl spiperone | CH$_3$ | H | H |
| N-fluoroethyl spiperone | CH$_2$CH$_2$F | H | H |
| N-fluoropropyl spiperone | CH$_2$)$_3$F | H | H |
| 2'-iodo-spiperone | H | I | H |
| 4-iodo-spiperone | H | H | I |
| 4-bromo-spiperone | H | H | Br |

Recently, several patents describing the synthesis and pharmacological studies of bicyclic benzamide analogs have been reported. (Lednicer, D., Sun, J. H. Eur. Pat. Appl. EP 147044 A2, Jul. 3, 1985; Florvall, L., Johansson, L., Kumar, Y., DePaulis, T., Ogren, S. Brit. UK Pat. Appl. GB 2176785 A1, 7 Jan. 1987). Of particular interest is the dihydrobenzofuran series, the bromo and chloro derivatives have displayed high pharmacological potential and good receptor affinity in an in vitro binding assay. Still, there is a need for new iodinated D-2 dopamine receptor imaging agents with higher receptor affintiy (longer retention time in the brain for data accumulation and less in vivo metabolism).

SUMMARY OF THE INVENTION

Test results indicate that the novel compounds of Formulas I and II are highly selective for the CNS D-2 receptor and should therefore possess utility as imaging agents for evaluation of such receptors.

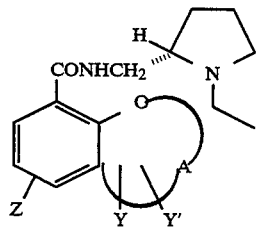
Formula I

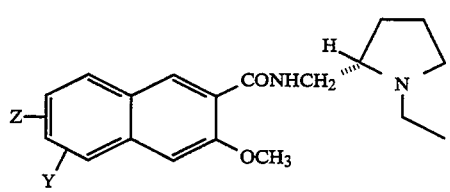
Formula II where

Y and Y' are independently selected from the group consisting of hydrogen and any hydrocarbon moiety which will not substantially interfere with the molecular binding of the molecule to the dopamine receptor target;

Z is selected from the group consisting of H, halogen (Hal), C=CH—Hal; $C_1$–$C_{10}$ alkylene-Hal; $C_1$–$C_{10}$ alkylene-C=CH—Hal; $C_1$–$C_{10}$ alkylene-phenyl-Hal; or Cl–C10 alkylene-heteroaryl-Hal; provided that, in Compounds of Formula I, Z is other than Cl, Br or F; and A is an alkylene moiety of from two to eight carbon atoms.

This invention therefore relates to the novel compounds of Formulas I and II, to methods of preparing them and to methods of utilizing them as imaging agents for the evaluation of CNS D-2 receptors. This invention further relates to novel compounds of Formulas III and IV which are useful as intermediates for preparing the novel compounds of Formulas I and II.

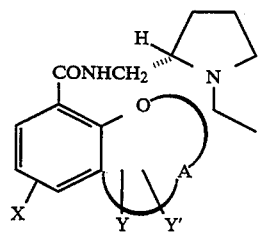
Formula III

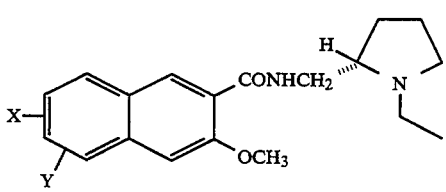
Formula IV where

X is selected from the group consisting of $Sn(R)_3$, $Si(R)_3$ and HgR;

R is $C_1$–$C_5$ alkyl;

Y and Y' are independently selected from the group consisting of hydrogen and any hydrocarbon moiety which will not substantially interfere with the molecular binding of the molecule to the dopamine receptor target; and A is an alkylene moiety of from two to eight carbon atoms.

DETAILED DESCRIPTION OF THE INVENTION

Figure 1:
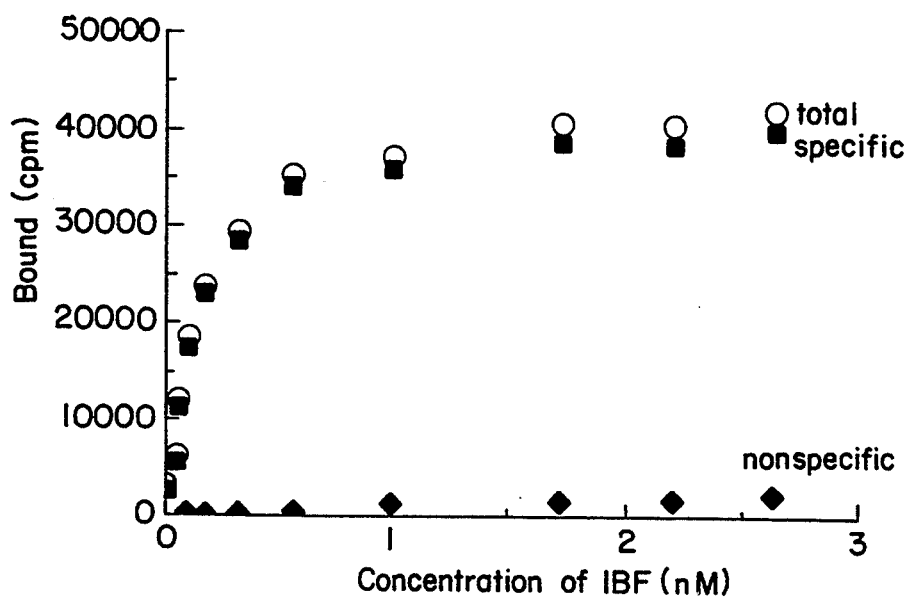
FIG. 1 is a saturation curve for the compound (IBF) showing low nonspecific binding for the compound 5-iodo-7-N-[(ethyl-2-pyrrolidinyl)methyl]carboxamido-2,3-dihydrobenzofuran (IBF) to rat striatal homogenate in vitro.

The novel compounds of Formulas I–IV all contain the N-ethyl-2-(aminomethyl)pyrroldine moiety. In general, such compounds can be prepared by coupling the pyrrolidine compound with the acid chloride derivatives of the desired dehydrobenzofuran or naphthalene as reported previously for the compound IBZM. (Kung, H. F., Kasliwal, R., Pan, S., Kung, M.-P., Mach, R. H., Guo, Y.-Z. J. Med. Chem. 1988, 31, 1039).

Naphthamide compounds of Formulas II and IV can be prepared by methods as illustrated in Schemes 1–3, or methods analogous thereto. The synthesis of both the 7-Br and 7-I naphthyl amides, 5 and 8 respectively, is outlined in Scheme 1.

Scheme 1

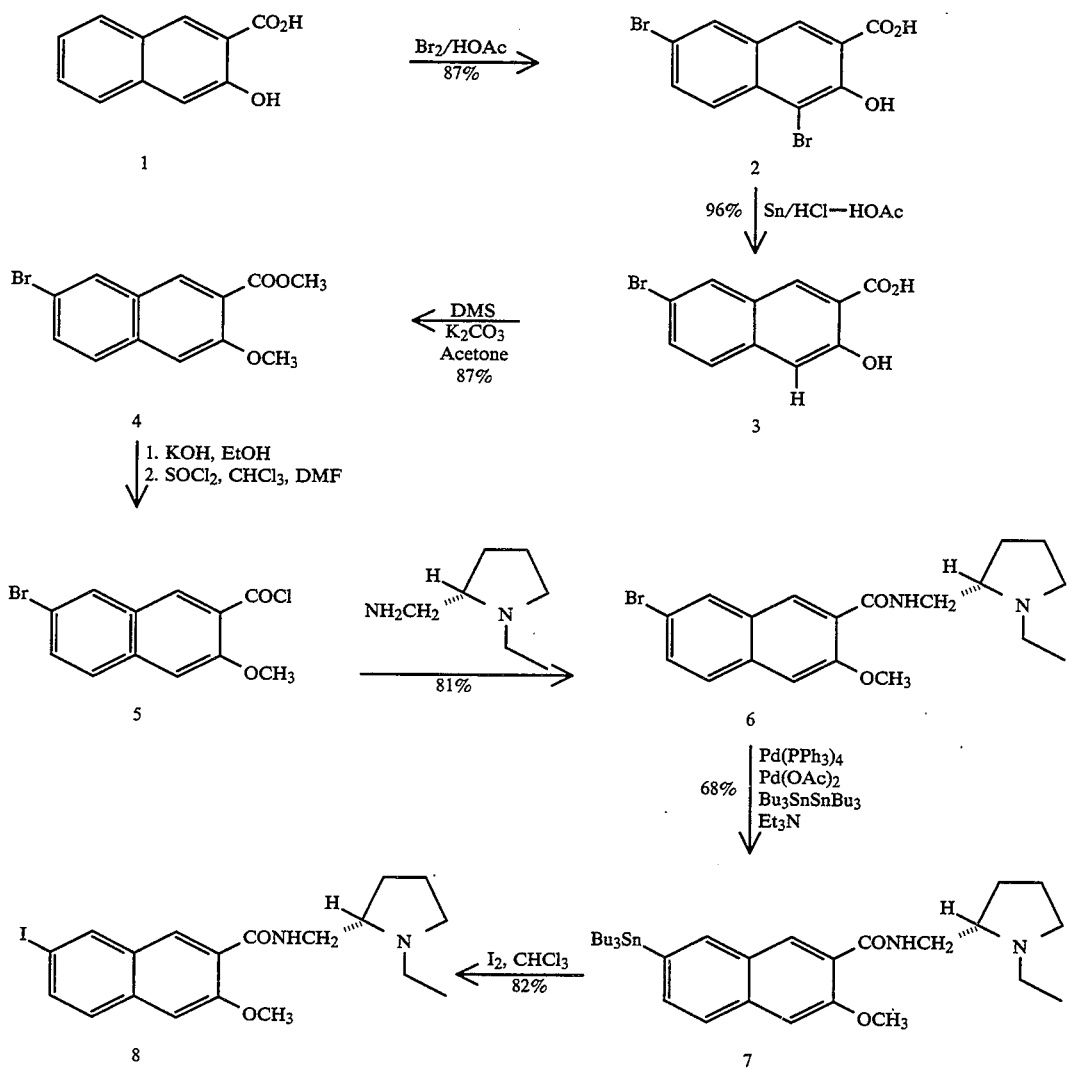

Treatment of 3-hydroxy-2-naphthoic acid 1 with excess bromine in glacial acetic acid gives the 4,7-dibromohydroxy acid, 2, in good yield. The dibromo acid, 2, is selectively debrominated at the 4-position using tin and acid to afford a high yield of the 7-bromonaphthoic acid, 3. The methoxy ester compound, 4, is prepared by refluxing hydroxy acid, 3, in acetone with two equivalents of dimethyl sulfate and excess powdered anhydrous potassium carbonate. Ester, 4, is hydrolysed to the corresponding methoxy acid using ethanolic hydroxide, and the acid is then cleanly converted to the corresponding acid chloride, 5, with thionyl chloride in dry chloroform containing a catalytic amount of dimethyl formamide. Condensation of the 7-bromonaphthoylchloride, 5, with (S)-(−)-2-(aminomethyl)pyrrolidine in chloroform gave the desired amide, 6, in 81% yield. The 7-iodo compound, 8, was then synthesized from this bromo amide, 6, via the intermediacy of a stable, versatile tin intermediate. The halide interconversion began with a palladium catalysed exchange of the aryl bromide with tributyl tin in refluxing dry triethylamine using tetrakistriphenylphosphine palladium to afford (Azizian, H., Eaborn, C., Pidock, A. J. Organometal. Chem. 1981, 215, 49) to afford the 7-tributylstannyl amide, 7, in acceptable yield. (Analogously, intermediates in which X is Si(R)$_3$ or HgR could be prepared by reaction with R$_3$SiSiR$_3$ or RHgCl.) Stannyl amide, 7, was then converted to the iodo derivative, 8, in 82% yield by simply stirring with iodine in dry chloroform at room temperature. Although the use of the tributylstannyl intermediate, 7, is illustrated in this scheme, other intermediates such as those within the scope of Formula IV may be used.

The synthesis of the naphthylamide analog, 11, which is unsubstituted at the 7-position, is shown in Scheme 2.

Scheme 2

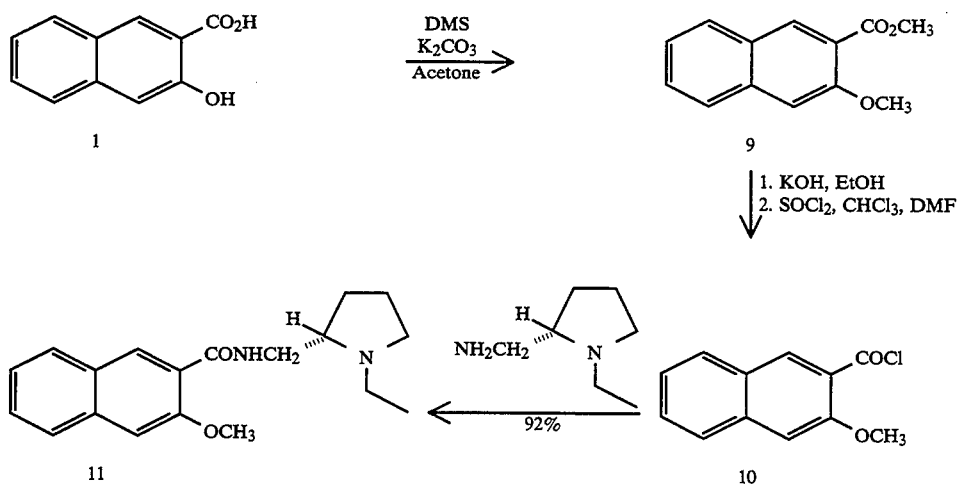

The synthesis illustrated in Scheme 2 begins with the same starting material as used in Scheme 1, 3-hydroxy-2-naphthoic acid, 1. Hydroxyacid, 1, is exhaustively methylated by refluxing with dimethyl sulfate and powdered anhydrous potassium carbonate in acetone to afford methoxyexter, 9. Ester, 9, is hydrolyzed to the corresponding acid and then converted directly to acid chloride, 10, with thionyl chloride in dry chloroform and a catalytic amount of dimethyl formamide. Condensation of the acid chloride, 10, with (S)-(−)-2-(aminomethyl)pyrrolidine in chloroform gives the desired parent naphthamide analog, 11.

The strategy employed in the synthesis of Compounds of Formulas I and III is illustrated in particularity for 5-Br and 5-I dihydrobenzofuranamides 19 and 21, respectively, in Scheme 3.

Scheme 3

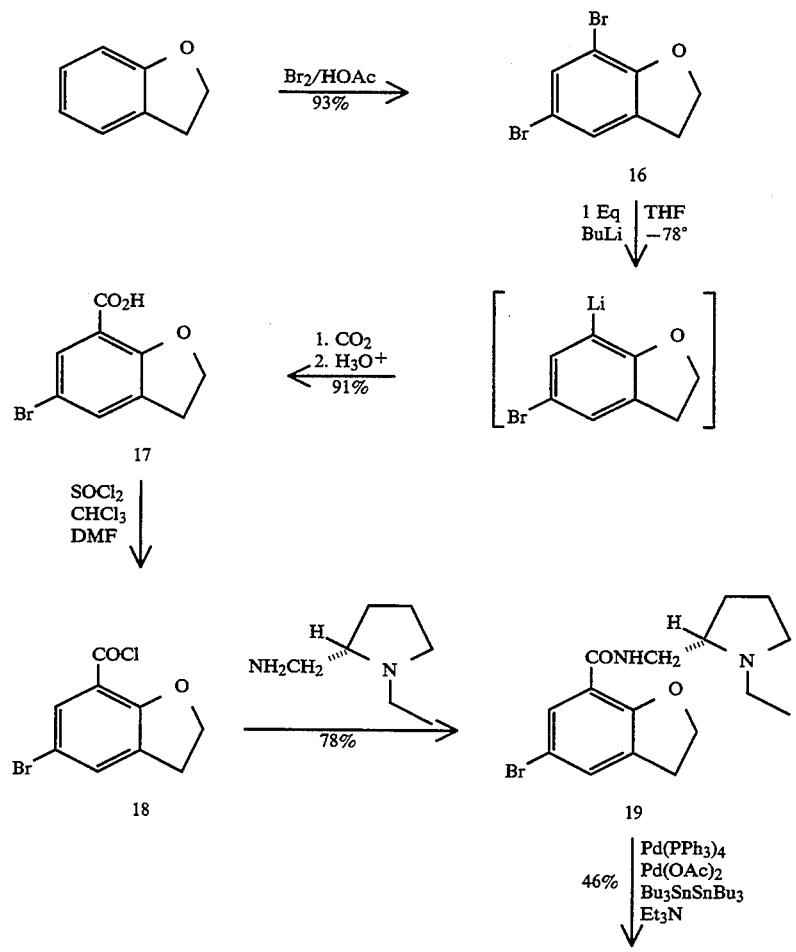

Scheme 3

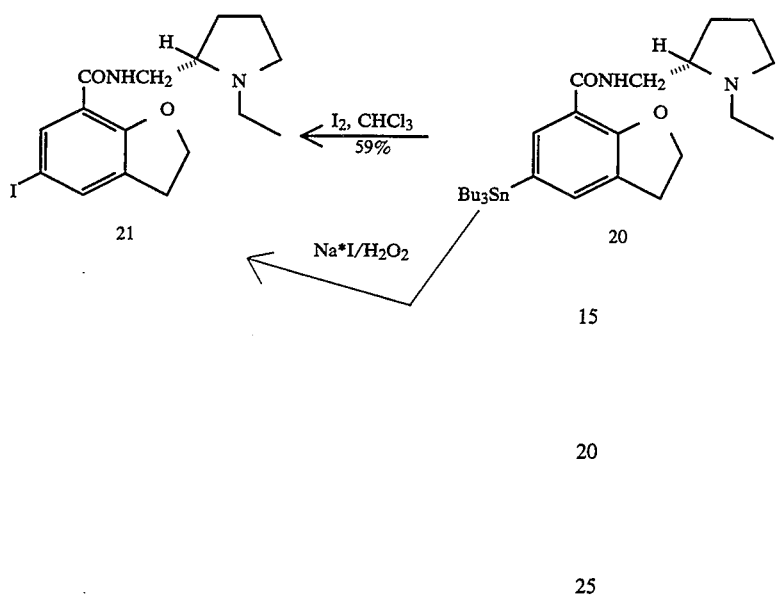

As illustrated in Scheme 3, 5,7-Dibromo-2,3-dihydrobenzofuran, 16, is obtained in excellent yield by treatment of 2,3-dehydrobenzofuran with 2.2 equivalents of bromine in cold glacial acetic acid. Taking advantage of the stabilizing effect of the furan oxygen atom, dibromobenzofuran, 16, is selectively lithiated at the 7-position with one equivalent of n-butyl lithium in dry tetrahydrofuran at −78° C. and then quenched with $CO_2$ and acid to afford 5-bromo-7-carboxy-2,3-dihydrobenzofuran, 17, in excellent yield. Conversion of bromoacid, 17, to the corresponding acid chloride, 18, is accomplished using thionyl chloride in refluxing chloroform with a catalytic amount of dimethyl formamide. The acid chloride is then condensed with (S)-(−)-2-(aminomethyl)pyrrolidine in chloroform to give the desired 5-bromobenzofuranamide, 19, in good yield. Conversion of the 5-bromo compound, 19, to the 5-iodo compound, IBF, 21, is accomplished as described for the naphthyl series through the intermediacy of a 5-stannyl derivative, 20. 5-Bromoacid, 19, is treated with the zero valent catalyst tetrakistriphenylphosphine palladium and hexabutyl ditin and refluxed in dry triethylamine for several hours to afford the isolatable, purifiable 5-tributylstannyl-benzofuranamide derivabive, 20, in moderate yield. (Analogously, intermediates in which X is $Si(R)_3$ or HgR could be prepared by reaction with $R_3SiSiR_3$ or RHgCl.) The 5-iododihydrobenzofuran derivative, IBF, 21, is obtained from the tributylstannyl intermediate simply by stirring with iodine in chloroform at room temperature.

The synthesis of the unsubstituted dihydrobenzofuranamide analog, 23, outlined in Scheme 4, proceeds from 2,3-dihydrobenzofuran.

Scheme 4

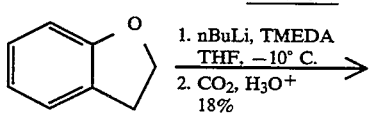

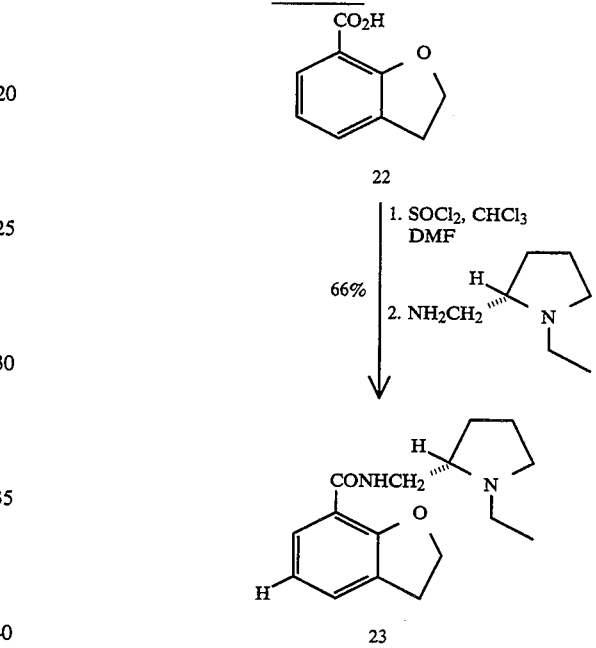

As illustrated in Scheme 4, direct, selective lithiation of dihydrobenzofuran at the 7-position is achieved by treatment with n-butyllithium in TMEDA/tetrahydrofuran at −23° C. Quenching of the reaction mixture after twenty minutes with $CO_2$ and acid affords the desired 7-carboxyfuran, 22. The carboxylic acid is converted to the corresponding acid chloride with thionyl chloride in chloroform-dimethyl formamide, and then condensed with (S)-(−)-2-(aminomethyl)pyrrolidine in chloroform to give the unsubstituted benzofuranamide, 23.

Radiolabeled compounds of the invention may be prepared by subjecting an intermediate compound of Formula III or IV to an electrophilic radiohalogenation reaction using hydrogen peroxide as the oxidant. Although $^{125}$I-isotopes are useful for laboratory testing, they will generally not be useful for actual diagnostic purposes because of the relatively long half-life (60 days) and low gamma-emission (30–65 Key) of [125]I. The isotope $^{123}$I has a half life of thirteen hours and gamma energy of 159 KeV, and it is therefore expected that labeling of ligands to be used for diagnostic purposes would be with this isotope. Other isotopes which may be used include [131]I (half life of 2 hours).

Substituents Y and Y' in the compounds of this invention are generally hydrogen or any hydrocarbon moiety which will not substantially interfere with the binding of the molecule to dopamine receptor targets. Examples of such substituents include but are not limited to $C_1$-$C_5$ alkyl, $C_1$-$C_5$ alkenyl and $C_1$-$C_5$ alkynyl groups.

Preferred compounds of this invention are those of Formula I wherein, independently or in combination, (1) A is —$CH_2$—$CH_2$—; (2) Y and Y' are H; (3) Z is in the 5-position; (4) Z=I, $^{123}$I, $^{125}$I or $^{131}$I. Also preferred are those compounds of Formula II wherein, independently or in combination, (1) Y is H; (2) Z is in the 7-position. The most preferred compound of the invention is compound 21, 5-iodo-7-N-[(1-ethyl-2-pyrrolidinyl)methyl]carboxamido-2,3-dihydrobenzofuran, also referred to herein as "IBF".

Specific examples of compounds contemplated within the scope of this invention are presented in Tables 3 and 4.

TABLE 3

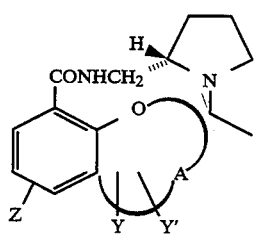

| Y | Y' | Z | A |
|---|---|---|---|
| H | H | 5-I | —$CH_2CH_2$— |
| H | H | H | —$CH_2CH_2$— |
| H | H | 5-CH=CHI | —$CH_2CH_2$— |
| H | H | 5-CH=CHBr | —$CH_2CH_2$— |
| H | H | 5-CH=CHCl | —$CH_2CH_2$— |
| H | H | 5-$CH_2$I | —$CH_2CH_2$— |
| H | H | 5-$CH_2CH_2$I | —$CH_2CH_2$— |
| H | H | 5-$CH_2$CH=CHI | —$CH_2CH_2$— |
| H | H | 5-$CH_2$—Ph—I | —$CH_2CH_2$ |
| H | H | 4-CH=CHI | —$CH_2CH_2$— |
| H | H | 4-CH=CHBr | —$CH_2CH_2$— |
| H | H | 4-CH=CHCl | —$CH_2CH_2$— |
| H | H | 4-$CH_2$I | —$CH_2CH_2$— |
| H | H | 4-$CH_2CH_2$I | —$CH_2CH_2$— |
| H | H | 4-$CH_2$CH=CHI | —$CH_2CH_2$— |
| H | H | 4-$CH_2$—Ph—I | —$CH_2CH_2$— |
| H | H | 4-I | —$CH_2CH_2$— |
| H | H | 6-I | —$CH_2CH_2$— |
| H | H | 5-I | —$CH_2CH_2CH_2$— |
| H | H | 5-I | —$CH_2CH_2$—$CH_2CH_2$— |
| 4-$CH_3$ | H | 5-I | —$CH_2CH_2$— |
| H | 3-$CH_3$ | 5-I | —$CH_2CH_2$— |
| 6-CH=$CH_2$ | H | 5-I | —$CH_2CH_2$— |
| H | 2-CH=$CH_2$ | 5-I | —$CH_2CH_2$— |

TABLE 4

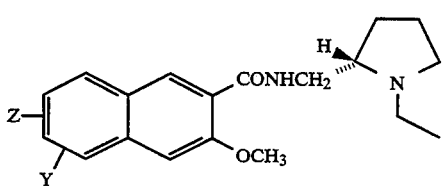

| Y | Z |
|---|---|
| H | 7-I |
| H | 7-Br |
| H | 7-Cl |
| H | H |
| H | 6-I |
| H | 6-Br |
| H | 6-Cl |
| H | 7-$CH_2$I |
| H | 7-$CH_2$Br |

TABLE 4-continued

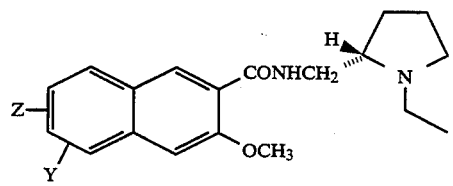

| Y | Z |
|---|---|
| H | 7-$CH_2$Cl |
| H | 7-CH=CHI |
| H | 7-CH=CHBr |
| H | 7-CH=CHCl |
| 6-$CH_3$ | 7-Br |
| 5-$CH_3$ | 7-Br |
| 6-CH=$CH_2$ | 7-Br |
| 8-CH=$CH_2$ | 7-Br |

The affinity of compounds of this invention for D-2 dopamine receptors was studied using in vitro competetive binding assays. Competition binding data using [$^{125}$I]IBZM are presented in Table 5.

TABLE 5

| Inhibition Constants of Various Compounds on [$^{125}$I]IBZM Binding to Rat Striatal Membranes* | |
|---|---|
| Compound** | Ki (nm, mean ± SEM) |
| 6 | 82.0 ± 12 |
| 8 | 168 ± 13 |
| 11 | 30.0 ± 4.2 |
| 19 | 3.89 ± 0.62 |
| 21 | 0.33 ± 0.02 |
| 23 | 135 ± 22 |
| Comparative Cpd. A*** | 280 ± 47 |

TABLE 5-continued

Inhibition Constants of Various Compounds on [125I]IBZM Binding to Rat Striatal Membranes*

| Compound** | Ki (nm, mean ± SEM) |
|---|---|
| Comparative Cpd. B*** | 507 ± 29 |

*0.15–0.4 nM [125I]IBZM was incubated in the presence of the indicated compounds in 7–11 concentrations and of membrane preparation from rat striatum. Each value represents the mean ± SEM of three to five determinations.
**Compound numbers refer to compounds as numbered in Schemes 1–4.
***Comparative Compound A is the hydroxynaphthylamide,

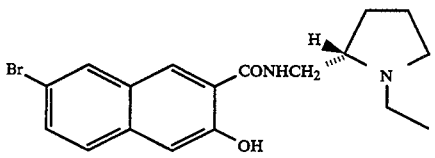

and Comparative Compound B is the isonaphthylamide

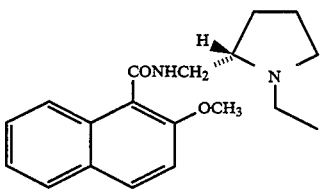

As the data in Table 5 indicate, in the naphthalene series, the rank order of potency is —H(11)>—Br (6)>—I (8); Ki (nM) values are 30.0, 82.0 and 168.0, respectively. The data suggest that the bulk tolerance of the D-2 dopamine receptor binding for this part of the molecule is limited. The results from the same binding study for a 3-hydroxynaphthamide analog and a 2-methoxy-1-naphthylamide (Comparative Compounds A and B) show the degree to which slight structural changes can affect receptor affinity.

The benzofuran series display high binding affinity. The Ki values for —H (23), —Br (19) and —I (21) are 135, 3.89 and 0.23 nM, respectively. Unexpectedly, the addition of an iodine atom appears to enhance the binding affinity significantly. The iodo group is apparently sixteen times more effective than the bromine atom for increasing the competitive binding affinity. This has not previously been reported for the dihydrobenzofuran derivatives. The data reported herein strongly suggest that the bulk tolerance in this part of the molecule, and perhaps the higher lipid-solubility, due to the presence of iodine, enhance binding.

Similarly to the high affinity reported previously for [125I]IBZM (Ref. 14), [125I]IBF, 21, competetively bound to rat striatal homogenate in vitro. The saturation curve shown in FIG. 1 displays an extremely low nonspecific binding (5% at $K_d$). The specific binding of [125I]IBF was found to be saturable and displayed a Kd of 0.106±0.015 nM. This value is lower than that of [125I]IBZM ($K_d$=0.426 mM) measured under similar conditions. Competition data of various receptor ligands for [125I]IBF binding are listed in Table 6, showing the following rank order of potency: spiperone IBF>IBZM>(+)butaclamol>(±)ADTN, 6,7>ketanserin>SCH-23390>propanolol. The results confirm that [125I]IBF binds specifically and selectively to the dopamine D-2 receptor.

TABLE 6

Inhibition Constants of Various Compounds on 125I]IBF Binding to Rat Striatal Membranes*

| Compound | ki (nM, mean ± SEM) |
|---|---|
| Spiperone | 0.015 ± 0.002 |
| S (—) IBZM | 0.261 ± 0.018 |
| S (—) IBF | 0.085 ± 0.010 |
| (+) Butaclamol | 1.190 ± 0.14 |
| (+) ADTN,6,7 | 65.7 ± 13.0 |
| Ketanserin | 491 ± 49 |
| Dopamine | 843 ± 150 |
| SCH-23390 | 820 ± 164 |
| Propanolol | >10,000 |

*0.15–0.30 nM [125I]IBF was incubated in the presence of the indicated compounds in 7–11 concentrations and of membrane preparation from rat striatum. Each value represents the mean ± SEM of three to five determinations.

IBF, 21, was subjected to a detailed in vivo biodistribution study, the results of which are presented in Table 7.

TABLE 7

Biodistribution of [125I]IBF in Rats After IV Injection (% Dose/Organ, Average of 3 Rats ± SD)

| Organ | 2 min | 15 min | 30 min | 60 min | 120 min |
|---|---|---|---|---|---|
| Blood | 3.50 ± 0.22 | 1.80 ± 0.31 | 1.26 ± 0.10 | 0.98 ± 0.11 | 0.53 ± 0.02 |
| Heart | 0.81 ± 0.25 | 0.20 ± 0.03 | 0.11 ± 0.01 | 0.05 ± 0.002 | 0.02 ± 0.001 |
| Muscle | 11.25 ± 2.62 | 14.36 ± 1.29 | 9.00 ± 1.66 | 4.97 ± 0.56 | 2.30 ± 0.22 |
| Lung | 6.14 ± 1.19 | 1.85 ± 0.33 | 0.82 ± 0.08 | 0.37 ± 0.10 | 0.12 ± 0.02 |
| Kidney | 7.58 ± 0.66 | 2.92 ± 0.30 | 1.58 ± 0.46 | 1.01 ± 0.01 | 0.68 ± 0.32 |
| Spleen | 0.96 ± 0.08 | 0.58 ± 0.08 | 0.31 ± 0.03 | 0.09 ± 0.01 | 0.03 ± 0.007 |
| Liver | 16.32 ± 4.00 | 16.16 ± 7.54 | 11.59 ± 0.93 | 9.84 ± 1.50 | 3.95 ± 0.31 |
| Skin | 8.54 ± 1.21 | 8.46 ± 0.56 | 5.34 ± 0.17 | 2.38 ± 0.17 | 1.18 ± 0.18 |
| Thyroid | 0.06 ± 0.02 | 0.03 ± 0.004 | 0.02 ± 0.004 | 0.02 ± 0.01 | 0.08 ± 0.03 |
| Brain | 0.98 ± 0.15 | 0.54 ± 0.06 | 0.30 ± 0.05 | 0.17 ± 0.02 | 0.07 ± 0.006 |
| Brain* Blood | 2.64 ± 0.32 | 3.01 ± 0.91 | 2.26 ± 0.33 | 1.90 ± 0.29 | 1.53 ± 0.12 |

*% dose/gram ratio

As seen from the data in Table 7, after an intravenous injection, [125I]IBF, 21, showed good brain uptake in rats. The initial uptake (0.98% dose/organ) at two minutes after injection was lwer than that of [125I]IBZM (2.87% dose/organ). At later time points, the brain uptake decreased; at one hour after injection a large portion of the radioacivity had washed out from the brain (0.17% dose/organ). The brain washout pattern in rats was similar to that of [125I]IBZM.

High initial uptake in the lungs (6.14% dose/organ) was also observed, but it was rapidly cleared. At 30 and 120 minutes, the lung uptake dropped to 0.82% and 0.37%, respectively. Liver uptake remained high throughout the first hour and gradually declined at two hours postinjection. The relatively low thyroid uptake at one hour postinjection (0.02%) suggests that little or no in vivo deiodination of [1125I]IBF, 21, occurred. As compared with [125I]IBZM, which showed a thyroid uptake of 0.1% at one hour postinjection, the new iodinated D-2 agent, [125I]IBF, 21, containing an iodine atom at the aromatic ring without activated group, displays better in vivo stability.

Figure 2:
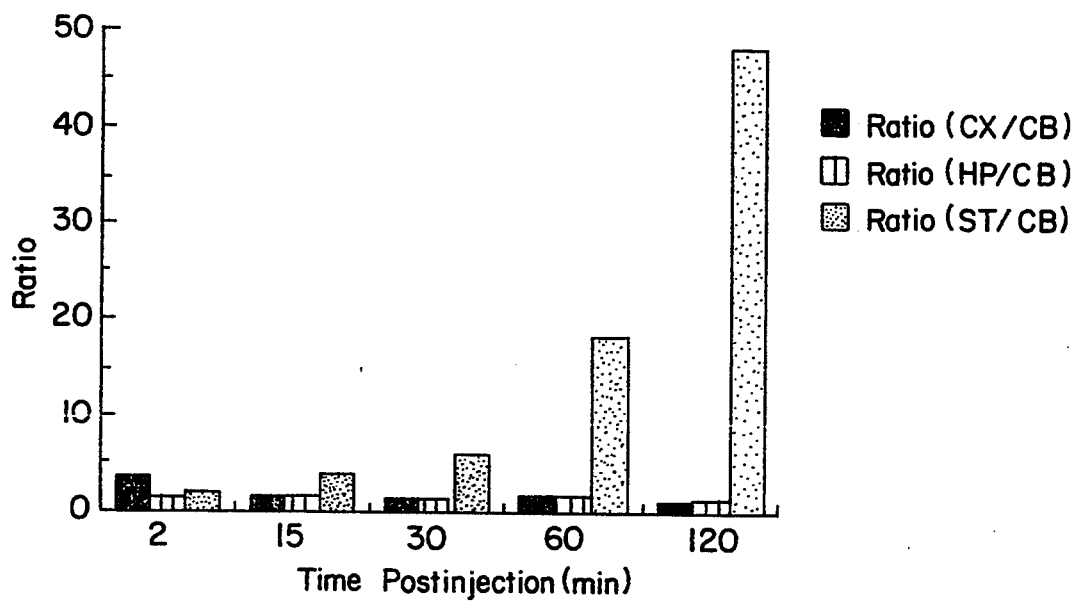
FIG. 2 is a bar graph showing ratios (based on % dose/gram) of regional cerebral uptake of [$^{125}$I]IBF (CX: cortex, ST: striatum, CB: cerebellum, HP: hippocampus).

Utilizing a brain regional dissection technique, the striatum/cerebellum (ST/CB) ratio (target to nontarget ratio) displayed a dramatic increase with time; 2.0, 3.8, 6.2, 18 and 48 at 2, 15, 30, 60 and 120 minutes, respectively. (See FIG. 2). This type of profound increase in target to nontarget ratio versus time was not observed for the other two regions (hippocampus and cortex) (FIG. 2). These results suggest that in regions with nonspecific association, i.e., regions low in dopamine receptors, the agent is washed out rapidly; whereas the straitum (rich in dopamine receptors) shows prolonged retention. A preliminary study on ex vivo autoradiography of this compound also confirms the high striatal uptake and low cerebellar activity. The data have been further confirmed by an in vivo imaging study of a monkey. The planar images displayed a high uptake and retention in the basal ganglia, where the CNS D-2 dopamine receptors are located.

The above-described test results indicate that compounds [$^{125}$I]IBF displays in vivo and in vitro properties superior to those of [$^{125}$I]IBZM and suggest that the compound and the structurally related compounds encompassed by Formulas I and II, should when appropriately labeled be useful imaging agents for imaging D-1 receptors in the living human brain using well-known methods such as SPECT The compound IBF, when labeled with $^{125}$I displays in vivo and in vitro properties comparable to those for [$^{125}$I]IBZM. The in vivo stability and high target to nontarget ratio, coupled with the extremely low nonspecific binding in vitro, suggest that IBF is superior to IBZM as a D-2 binding agent for pharmacological evaluations. By virtue of their D-2 receptor capability, the novel compounds of Formulas I and II way also possess as yet undefined therapeutic value.

The preparation and testing of the compounds of this invention are discussed in more detail in the following examples which are not intended to limit the scope of this invention. In all examples, Proton NMR was recorded on a Varian EM 360A spectrometer. The chemical shifts were reported in ppm downfield from an internal tetramethylsaline standard. Melting points were determined on a Meltemp apparatus are reported uncorrected. Elemental analyses were performed by Atlantic Microlabs, Inc., of Norcross, Ga. and were within 0.4% of the theoretical values.

EXAMPLE 1

4,7-Dibromo-3-hydroxy-2-naphthoic acid (2).

3-hydroxy-2- naphthoic acid (1) (10 g, 0.053 mol) was suspended in glacial acetic acid (100 mL) and cooled to 0° C. To this mechanically stirred mixture was added dropwise a solution of bromine (21 g, 0.133 mol) in glacial acetic acid (50 mL) so as to maintain the reaction temperature below 5° C. Following the addition, the reaction mixture was refluxed for 2 h, cooled and poured into ice water (1000 mL). The solid dibrominated product was filtered, washed with water (3×100 mL) and ether (100 mL) and air dried to afford a bright yellow solid (16 g, 87%). $^1$H NMR (CDCl$_3$)δ8.45(1 H,s), 8.3(phenol OH,bs), 8.05(1 H,d), 7.81(1 H,s), 7.76(1 H, d).

EXAMPLE 2

7-Bromo-3-hydroxy-2-naphthoic acid (3).

Dibromo acid (2 ) (7 g, 0.02 mol ) was suspended in glacial acetic acid (100 mL) and 12N HCl (25 mL) and mossy tin (2.3 g, 0.02 mol) was added. The reaction mixture was heated at reflux for three h, cooled and diluted with water (100 mL). The yellow solid product was filtered, washed with water (3×100 mL) and air dried to afford the 7-bromo compound(3) (5.1 g, 96%). $^1$H NMR(CDCl$_3$)δ8.38 (1 H,s), 7.95(1 H,s), 7.5(2 H,d), 7.16(1 H,s). The low resolution mass spectrum showed an M+ peak m/e 280. Anal. (C$_{11}$H$_7$O$_3$Br) C,H.

EXAMPLE 3

7-Bromo-3-methoxy-2-methylnaphthoate (4 ).

Bromo acid (3 ) (5.0 g, 0.018 mol), powdered, anhydrous potassium carbonate (12 g), and dimethyl sulfate (4.5 g, 0.041 mol) in dry acetone were refluxed for 4 h. The reaction mixture was cooled and water (5 mL) was added and stirred for 2 h to destroy any remaining dimethyl sulfate. The inorganic material was filtered and the acetone was removed under reduced pressure. The residue was taken up in methylene chloride, washed several times with water, dried over anhydrous magnesium sulfate, filtered and concentrated to afford the methoxy ester (4) (4.6 g, 87%). $^1$H NMR (CDCl$_3$) δ8.21 (1 H,s), 7.79(1 H,s), 7.38(2 H,s), 7.1(1 H,s), 3.92(3 H,s), 3.87(3 H,s).

EXAMPLE 4

7-Bromo-3-methoxy-2-naphthoic acid.

The ester (4 ) (4.0 g, 0.0136 mol) was dissolved in ethanolic sodium hydroxide and heated to reflux for 2 h. The reaction mixture was cooled and the ethanol removed under reduced pressure. The sodium salt of the acid was treated with 2N HCl and stirred for 20 min, filtered, washed with water (3×50 mL) and air dried to afford the acid product as a white solid (3.5 g, 92%). $^1$H NMR(CDCl$_3$)δ9.1(OH,bs), 8.55(1 H,s), 7.92(1 H, s), 7.6(2 H,s), 7.21(1 H,s), 4.11(3 H,s).

EXAMPLE 5

7-Bromo-3-methoxy-2-naphthoic acid chloride(5).

The acid prepared above (1 g, 0.0036 mol) was dissolved in dry chloroform (25 mL) and treated with thionyl chloride (1.27 g, 0.01 mol) and catalytic amount of N,N-dimethyl-formamide. The reaction mixture was refluxed for 3 h and the solvent removed under reduced pressure. The residue was dissolved in toluene (25 mL) and concentrated again to remove any remaining thionyl chloride. $^1$H NMR(CDCl$_3$)δ8.36(1 H,s), 7.9(1 H,s), 7.51(2 H,s), 7.05(1 H,s), 3.95(3 H,s).

EXAMPLE 6

S-(—)-7-Bromo-3-methoxy-N[(1-ethyl-2-pyrrolidinyl)-methyl]naphthyl-2-carboxamide(6).

The acid chloride (5) prepared as described above was dissolved in chloroform (25 mL) and added slowly, dropwise, to a solution of excess S-(—)-2 -aminomethyl-N-ethyl pyrrolidine. The reaction was stirred at room temperature for 1 h and then concentrated in vacuo to afford a yellow oily product. The oil was dissolved in 2N HCl and the pH of the solution was then carefully adjusted to 7. The product was extracted into chloroform (3×30 mL), dried over anhydrous magnesium sulfate, filtered and rotary evaporated to afford a yellowish solid product. The product was chromatographed on silica gel [methylene chloride-methanol(8:2)] to afford a whitish solid (1.15 g, 81%). $^1$H NMR(CDCl$_3$)δ8.59(1 H, s), 8.5(NH,bs), 7.9(1 H,s), 7.5(2 H,s), 4.0(3 H,S), 2.5–3.8(11 H,m), 1.25(3 H,t); IR(-film) 3390(NH), 1650(CO). Anal. Calcd (Cl high resolution mass spectrum) for $C_{19}H_{23}N_2O_2Br(M+H)$ 391.1024, found 391.1021. Anal. $(C_{19}H_{23}N_2O_2Br)$ C,H.

EXAMPLE 7

7-tri-Butylstannyl-3-methoxy-N-(1-ethyl-2-pyrrolidinylmethyl)naphthyl-2-carboxamide (7).

Bromo compound (6) (0.8 g, 0.002 mol), hexabutyl di-tin (1.4 g, 0.0024 mol), palladium (II) acetate (0.05 g, $2\times10^{-4}$ mol, 0.1 eq), and tetrakis triphenylphosphine palladium(0)(0.120 g, $1\times10^{-4}$ mol, 0.05 eq) were placed in a flame-dried flask equipped for reflux under argon and dissolved in dry triethylamine (distilled from calcium hydride and stored over potassium hydroxide)(30 mL). The reaction mixture was heated at 85° C. under argon for 2.5 h, cooled, and the solvent removed in vacuo to afford a black oil. The crude product was dissolved in methylene chloride (100 mL) and filtered through celite to remove precipitated palladium metal. The filtrate was concentrated and the yellow oily residue purified on silica gel. The column was eluted initially with chloroform to remove excess hexabutyl ditin and phosphines and then 10% methanolic chloroform was added to elute the pure product which upon removal of solvent appeared as a yellow oil (0.4 g, 68%). $^1$H NMR(CDCl$_3$)δ8.55(NH), 7.8(1 H,s), 7.45(2 H,s), 7.0(1 H,s), 4.0(3 H,s), 3.8–1.8(11 H,m), 1.7–0.8(30 H,m). The low resolution mass spectrum showed the M+ peak m/e 614.

EXAMPLE 8

(S)-(−)-7-Iodo-3-methoxy-N-[(1-ethyl-2-pyrrolidinyl)-methyl]naphthyl-2-carboxamide(8).

Tin compound (7) (0.3 g, $5\times10^{-4}$ mol) was dissolved in dry chloroform (30 mL), treated with iodine (0.8 g, 0.003 mol) and stirred at room temperature overnight under argon. The excess iodine was quenched with a 10% aqueous sodium thiosulfate solution, the organic layer washed with water (2×25 mL) and dried over anhydrous sodium sulfate. The solvent was removed to afford the crude product as a yellow oil which was purified on silica gel to afford the iodo product (0.180 g, 82%). $^1$H NMR(CDCl$_3$)δ8.6(1 H,s), 7.81(1 H,s) 7.45 (2 H,s) 7.05(1 H,s) 4.04(3 H, s) 3.8–1.7(11 H,m), 1.7–0.7(30 H,m). Anal. Calcd (Cl high resolution mass spectrum), for $C_{19}H_{23}O_2I(M+H)$ 439.0886, found 439.0882.

EXAMPLE 9

3-Methoxy-2-naphthoic Acid Chloride (10).

The acid (3 g, 0.016 mol), prepared by hydrolysis of the methyl ester was dissolved in dry chloroform (100 mL) and treated with thionyl chloride (3.7 g, 0.031 mol) and catalytic amount of N,N-dimethylformamide. The reaction mixture was refluxed for 3 h and the solvent removed under reduced pressure. The residue was dissolved in toluene (25 mL) and concentrated again to remove any remaining thionyl chloride.

EXAMPLE 10

(S)-(−)-3-Methoxy-N-[(1-ethyl-2-pyrrolidinyl)methyl]-naphthyl-2-carboxamide(11).

The acid chloride (10) prepared as described above was dissolved in chloroform (30 mL) and added slowly, dropwise, to a solution of excess 2-aminomethyl-N-ethyl pyrrolidine. The reaction was stirred at room temperature for 1 h and then concentrated in vacuo to afford a yellow oily product. The oil was dissolved in 2N HCl and the pH of the solution was then carefully adjusted to 7. The product was extracted into chloroform (3×30 mL), dried over anhydrous magnesium sulfate, filtered and rotary evaporated to afford a yellowish solid product. The product was chromatographed on silica gel [methylene chloridemethanol(8:2)] to afford a brown oil (4.6 g, 92%). $^1$H NMR (CDCl$_3$)δ8.55(1 H,s), 8.3(NH), 7.8–7.1(4 H,m), 7.03(1 H,s), 3.91(3 H,s), 3.8– 1.6(11 H,m), 1.08(3 H,t); IR(film) 3350(NH), 1660(CO). Anal. Calcd (Cl high resolution mass spectrum) for $C_{19}H_{24}N_2O_2(M+H)$ 313.1919, found 313.1916.

EXAMPLE 11

7-Bromo-3-hydroxy-naphthoic Acid Chloride(12).

Hydroxy acid (3) (2.0 g, 0.0075 mol) was suspended in dry chloroform (50 mL) and treated with thionyl chloride (2.6 g, 0.023 mol) and sufficient N,N-dimethylformamide to solubilize the hydroxy acid. The reaction mixture was refluxed for 3 hr and then the chloroform was removed under reduced pressure. The residue was dissolved in toluene (25 mL) and concentrated again to remove all thionyl chloride. The gummy solid acid chloride was used directly in the condensation reaction without purification.

EXAMPLE 12

(S)-(−)-7-Bromo-3-hydroxy-N-[(1-ethyl-2-pyrrolidinyl)methyl]naphthyl-2-carboxamide (13).

The acid chloride (12) prepared as described above was dissolved in chloroform (25 mL) and added slowly, dropwise to excess 2-aminomethyl-N-ethylpyrrolidine. The reaction mixture was stirred at room temperature for 2 h and concentrated in vacuo. The residue was dissolved in 2N HCl and then the pH was carefully adjusted to 7. The product was extracted into chloroform (3×50 mL), dried over anhydrous magnesium sulfate, filtered and concentrated in vacuo to afford a yellow oil. The oil was purified by silica gel chromatography [methylene chloride-methanol(9:1)] to afford a golden solid (2.43 g, 86%). $^1$H NMR(CDCl$_3$)δ9.3(OH,bs), 8.21(1 H, s), 7.9(1 H,s), 7.42(2 H,s), 7.18(1 H,s), 2.6–3.7 (11 H,m), 1.38 (3 H,t); IR(film) 3270(NH), 1660(CO). Anal. Calcd (Cl high resolution mass spectrum) for $C_{18}H_{21}N_2O_2Br(M+H)$ 378.0868, found 378.0864. Anal. $(C_{18}H_{21}N_2O_2Br)$ C,H.

EXAMPLE 13

2-Methoxy-1-naphthoic Acid Chloride(14).

2-Methoxy-1-naphthoic acid (3 g, 0.016 mol) was dissolved in dry chloroform (100 mL) and treated with thionyl chloride (3.7 g, 0.031 mol) and catalytic amount of N,N-dimethyl-formamide. The reaction mixture was refluxed for 3 h and the solvent removed under reduced pressure. The residue was dissolved in toluene (25 mL) and concentrated again to remove any remaining thionyl chloride.

EXAMPLE 14

2-Methoxy-N-[(1-ethyl-2-pyrrolidinyl)methyl]naphthyl-1-carboxamide(15).

The acid chloride (14) prepared as described above was dissolved in chloroform (30 mL) and added slowly, dropwise, to a solution of excess 2-aminomethyl-N-ethyl pyrrolidine. The reaction was stirred at room temperature for 1 h and then concentrated in vacuo to afford a yellow oily product. The oil was dissolved in 2N HCl and then the pH of the solution was carefully adjusted to 7. The product was extracted into chloroform (3×30 mL), dried over anhydrous magnesium sulfate, filtered and rotary evaporated to afford a yellowish solid product. The product was chromatographed on silica gel [methylene chloridemethanol(8:2)] to afford a brown oil (4.25 g, 85%). $^1$H NMR(CDCl$_3$)$\delta$7.8(1 H,d), 7.15(1 H,d), 7.9–7.3(4 H,m), 6.5(NH), 3.89(3 H,s), 3.8–1.6(11 H,m), 1.1(3 H,t); IR(film) 3350(NH), 1660(CO). Anal Calcd (Cl high resolution spectrum) for C$_{19}$H$_{24}$N$_2$O$_2$(M+H)313.1919, found 313.1916.

EXAMPLE 15

5,7-Dibromo-2,3-dihydrobenzofuran(16).

To a solution of 2,3-dihydrobenzofuran (10 g, 0.083 mol) in glacial acetic acid (100 mL) at 0° C., was added dropwise over a period of 30 rain bromine (40 g, 0.25 mol) in glacial acetic acid (50 mL). Following addition, the reaction mixture was stirred overnight at room temperature. Excess bromine was destroyed by addition of 10% sodium thiosulfate solution and the acetic acid was removed under reduced pressure. The oily residue was taken up in methylene chloride (150 mL), washed with a saturated sodium bicarbonate solution (3×50 mL), water (50 mL), and dried over anhydrous sodium sulfate. The solvent was removed in vacuo to afford a yellow oil (21.5 g, 93%). $^1$H NMR(CDCl$_3$)$\delta$7.28(1 H,s), 7.18(1 H,s), 4.6(2 H,t), 3.21(2 H,t). Anal. (C$_9$H$_7$O$_3$Br) C,H.

EXAMPLE 16

5-Bromo-7-carboxy-2,3-dihydrobenzofuran (17).

Dibromobenzofuran (16) (4 g, 0.014 mol) in dry tetrahydrofuran (distilled from sodium and benzophenone) was placed in a flame-dried flask under argon and cooled to −78° C. n-Butyl lithium (8.9 mL, 0.014 mol of a 1.6M hexane solution) was added to the reaction mixture dropwise via syringe. Immediately following the addition, carbon dioxide was bubbled through the reaction mixture and the solution was allowed to come to room temperature. The reaction was quenched with water and the solvent was removed in vacuo. To the residue was added 3N HCl(100 mL) and the mixture was stirred for 10 min. The solid product was filtered, washed with water, and air dried to afford carboxylic acid (17) (3.1 g, 91%). $^1$H NMR (CDCl$_3$)$\delta$7.65(1 H, s), 7.45(1 H,s), 5.62(2 H,t), 3.25(2 H,t). The low resolution mass spectrum showed the M+ peak at m/e 242.

EXAMPLE 17

5-Bromo-7-carboxy-2,3-dihydrobenzofuran Acid Chloride(18).

Carboxylic acid (17) (2.0 g, 0.0083 mol) was suspended in dry chloroform, treated with thionyl chloride (2.9 g, 0.0248 mol) and a catalytic amount of N,N-dimethyl-formamide, and refluxed for 2 h. The solvent was removed under reduced pressure and the semi-solid residue was dissolved in toluene (30 mL) and concentrated again to remove any remaining thionyl chloride.

EXAMPLE 18

5-Bromo-7-N-[(1-ethyl-2-pyrrolidinyl)methyl]carboxamido-2,3-dihydrobenzofuran(19).

The crude acid chloride (18) was dissolved in dry chloroform (25 mL) and added dropwise to an excess of (S)-2-aminomethyl-1-ethylpyrrolidine in chloroform (100 mL), and stirred at room temperature for 2 h. The chloroform was concentrated in vacuo and the residue dissolved in 2N HCl. The solution was carefully brought to pH 7 with 10% NaOH and the product extracted with chloroform (3×50 mL). The organic extracts were combined, dried and concentrated to afford a yellow oil which after purification on silica gel [methylene chloridemethanol (9:1)] gave a white solid product (19) (2.3 g, 79%). $^1$H NMR (CDCl$_3$)$\delta$7.85(1 H, s), 7.7(NH,bs), 7.15(1 H, s), 4.62(2 H,t), 3.5(2 H,m), 3.2 (2 H,t), 2.4–3.5(9 H,m), 1.05(3 H,t); IR(film) 3410, 3320(NH); 1655(CO). Anal. Calcd (Cl high resolution mass spectrum) for C$_{16}$H$_{21}$N$_2$O$_2$Br(M+H)353.0868, found 353.0864. Anal. (C$_{16}$H$_{21}$N$_2$O$_2$Br) C,H.

EXAMPLE 19

5-Tri-Butylstannyl-7-N-[(1-ethyl-2-pyrrol-idinyl)methyl]carboxamido-2,3-dihydrobenzofuran(20).

Bromo compound (19) (0.96 g, 0.0027 mol), hexabutyl ditin (1.87 g, 0.0032 mol), palladium (II) acetate (0.06 g, 3×10$^{-4}$ mol, 0.1 eq), and tetrakis triphenylphosphine palladium $^{39}$(0.150 g, 1×10$^{-4}$ mol, 0.05 eq) were placed in a flame-dried flask equipped for reflux under argon and dissolved in dry triethylamine (distilled from calcium hydride and stored over potassium hydroxide) (30 mL). The reaction mixture was heated at 85° C. under argon for 2.5 h, cooled, and the solvent removed in vacuo to afford a black oil. The crude product was dissolved in methylene chloride (100 mL) and filtered through celite to remove precipitated palladium metal. The filtrate was concentrated and the yellow oily residue purified on silica gel. The column was eluted initially with chloroform to remove excess hexabutyl ditin and phosphines and then 10% methanolic chloroform was added to elute the pure product which upon removal of solvent appeared as a yellow oil (0.710 g, 46%). $^1$H NMR(CDCl$_3$)$\delta$8.2(NH), 7.82(1 H,s), 7.29(1 H,s), 4.62(2 H,t), 3.2(2 H,t), 4.2–1.6(11 H,m), 1.5–0.8(30 H,m). The low resolution mass spectrum showed the M+ peak m/e 563.

EXAMPLE 20

5-Iodo-7-N-[(1-ethyl-2-pyrrolidinyl)methyl]carboxamido-2,3-dihydrobenzofuran,IBF(21).

Tin compound (20) (0.5 g, 9×10$^{-4}$ mol) was dissolved in dry chloroform (30 mL), treated with iodine (0.91 g, 0.0036 mol) and stirred at room temperature overnight under argon. The excess iodine was quenched with a 10% aqueous sodium thiosulfate solution, the organic layer washed with water (2×25 mL) and dried over anhydrous sodium sulfate. The solvent was removed to afford the crude product as a yellow oil which was purified on silica gel to afford the iodo product, 21, (0.210 g, 59%). $^1$H NMR(CDCl$_3$)$\delta$8.15(NH), 7.91(1 H,s), 7.32(1 H,s), 4.61 (2 H, t), 3.1 (2 H, t), 3.8–1.6(11 H,m), 1.27 (3 H,t). Anal Calcd (Cl high resolution mass spectrum) for $C_{16}H_{21}O_2I(M+H)401.0730$, found 401.0726.

EXAMPLE 21

7-Carboxy-2,3-dihydrobenzofuran(22).

To a stirred solution of 2,3-dihydrobenzofuran (1 g, 0.0083 mol) and dry TMEDA (1 eq.) in dry tetrahydrofuran (30 mL) at −10° C. under argon, was added n-BuLi (1.6M hexane solution) (5 mL, 0.008 mol). The reaction mixture was maintained at this temperature for 20 min and then carbon dioxide was bubbled through the reaction mixture as it warmed to room temperature. The reaction mixture was concentrated in vacuo to afford a yellow oil. The oil was dissolved in 10% sodium hydroxide (100 mL), washed with methylene chloride (2×25 mL), and acidified with HCl. The white solid product was filtered, washed with water and air-dried to afford the carboxylic acid (22) (0.22 g, 18%). $^1$H NMR (CDCl$_3$)δ7.35(1 H,d), 7.11(1 H,d), 6.59(1 H,t), 4.37 (2 H,t), 2.99(2 H,t).

EXAMPLE 22

7-N-[(1-ethyl-2-pyrrolidinyl)methyl]carboxamido-2,3-dihydrobenzofuran(23).

Carboxylic acid (22) was suspended in dry chloroform and treated with thionyl chloride (0.25 g, 0.002 mol) and several drops of dry DMF and the reaction mixture was refluxed for 2 h. The solvent was removed under reduced vacuum to afford the corresponding acid chloride as a yellow oil which was used directly in the condensation with the pyrrolidyl amine without purification.

The crude acid chloride was dissolved in dry chloroform (5 mL) and added dropwise to an excess of (S)-2-aminomethyl-1-ethylpyrrolidine in chloroform (25 mL), and stirred at room temperature for 2 h. The chloroform was concentrated in vacuo and the residue dissolved in 2N HCl. The solution was carefully brought to pH 7 with 10% NaOH and the product extracted with chloroform (3×25 mL). The organic extracts were combined, dried and concentrated to afford a yellow oil which after purification on silica gel [methylene chloride-methanol(9:1)] gave a thick clear oil (0.26 g, 66%). $^1$H NMR(CDCl$_3$)δ8.05 (NH), 7.72 (1 H, d), 7.15(1 H,d), 6.78 (1 H,d), 4.65(2 H,t), 3.15(2 H,t), 3.7–1.6(11 H,m), 1.14(3 H,t); IR(film) 3400(NH), 1650(CO). Anal Calcd (Cl high resolution mass spectrum) for $C_{16}H_{22}N_2O_2(M+H)275.1763$, found 275.1760.

Radiolabeling

Aqueous hydrogen peroxide (50 μL, 3% w/v) was added to a mixture of 50 μL of compound 20 (1 mg/mL EtOH), 50 μL 0.1N HCl and 5 μL of sodium [$^{125}$I]iodide (2–3 mCi, carrier-free, Sp. Act. 2,200 Ci/mmol) in a sealed vial. The reaction was allowed to proceed at 23° C. for 30 min, after which it was terminated by the addition of 0.1 ml of sodium bisulfite (300 mg/mL). The reaction mixture was neutralized via the addition of saturated NaHCO$_3$ solution and then extracted with ethyl acetate (3×1 mL). The combined organic layers were passed through an anhydrous sodium sulfate column (0.2cm×5cm), and evaporated to dryness by a stream of nitrogen. The residue was dissolved in 100% ethanol (50–100 μL), and the desired product, [$^{125}$I]IBF, 21, was isolated from the unreacted compound, 20, and a small amount of unknown radioactive impurities by HPLC using a reverse phase column (PRP-1, Hamilton Inc.) and an isocratic solvent of 90% acetonitrile/10% pH 7.0 buffer (5 mM, 3,3-dimethyl glutaric acid). The appropriate fractions were collected, condensed, and re-extracted with ethyl acetate (1×3 ml). The solution containing the no-carrier added product was condensed to dryness and redissolved into 100% ethanol (purity 99%, overall yield 75%). After dilution with saline, this agent was used for the in vivo and in vitro studies.

Biodistribution in Rats

Male Sprague Dawley rats (225–300 g), which were allowed free access to food and water, were used for in vivo biodistribution study. While under halothane anesthesia, 0.2 ml of a saline solution containing [$^{125}$I]IBF, 21, (8–10 μCi) was injected directly into the femoral vein, and the rats were sacrificed at various time points postinjection by cardiac excision under halothane anesthesia. The organs of interest were removed, weighed and the radioactivity was counted using a Beckman gamma automatic counter (Model 4000). The percent dose per organ was calculated by a comparison of the tissue counts to suitably diluted aliquots of the injected material. Total activities of blood and muscle were calculated assuming that they are 7% and 40% of total body weight, respectively.

Regional brain distribution in rats was obtained after an iv injection of [$^{125}$I]IBF, 21. By dissecting, weighing and counting samples from different brain regions (cortex, striatum, hippocampus and cerebellum), % dose/gram of samples was calculated by comparing the sample counts with the counts of the diluted initial dose. The uptake ratio of each region was obtained by dividing % dose/gram of each region with that ot the cerebellum.

Tissue Preparation

Male Sprague-Dawley rats (200–250 g) were decapitated, and the brains were removed and placed in ice. Striatal tissues were excised, pooled and homogenized in 100 volumes (w/v) of ice-cold Tris-HCl buffer (50 mM), pH 7.4. The homogenates were centrifuged at 20,000× g for 20 min. The resultant pellets were rehomogenized in the same buffer and centrifuged again. The final pellets were resuspended in assay buffer containing: 50 mM Tris buffer pH 7.4, 120 mM NaCl, 5 mM KCl, 2 mM CaCl$_2$ and 1 mM MgCl$_2$ and kept at −20° C. for the following binding assay.

Binding Assays

The binding assays were performed by incubating 50 μl of tissue preparations containing 40–60 μg of protein with appropriate amounts of l-125 labeled ligand and competitors in a total volume of 0.2 ml of the assay buffer. After an incubation period of 15 min at 37° C. (with stirring), the samples were rapidly filtered in the cell harvester (Brandel M-24R) under vacuum through Whatman GF/B glass fiber filters pretreated with 0.2% protamine base and washed with 3×5 ml of cold (4° C.) 50 mM Tris-HCl buffer, pH 7.4. The nonspecific binding was obtained in the presence of 10 μM spiperone. The filters were counted in a gamma counter (Beckman 5500) at an efficiency of 70%.

What is claimed is:

1. A compound selected from the group consisting of compounds of the formulas

Formula III

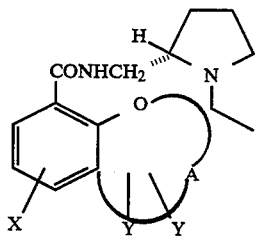

where
- X is selected from the group consisting of $Sn(R)_3$, $Si(R)_3$ and $HgR$;
- R is $C_1$–$C_5$ alkyl;
- Y and Y' are independently selected from the group consisting of hydrogen, $C_1$–$C_5$ alkyl, $C_2$–$C_5$ alkenyl and $C_2$–$C_5$ alkynyl groups; and
- A is an alkylene moiety of from two to eight carbon atoms.

2. A compound of claim 1 which has the Formula III.
3. A compound of claim 2 where A is —$CH_2CH_2$—.
4. A compound of claim 2 where each of Y and Y' is H.
5. A compound of claim 3 where X is in the 5-position.
6. A compound of claim 2 where X is $SnBu_3$.
7. A compound of claim 3 where each of Y and Y' is H.
8. A compound of claim 7 where X is in the 5-position.
9. A compound of claim 8 where X is $SnBu_3$.
10. The compound of claim 9 which is 5-tri-butylstannyl-7-N-[(1-ethyl-2-pyrrolidinyl)methyl]carboxamido-2,3-dihydrobenzofuran.
11. A compound of claim 3 where X is in the 4-position.
12. A compound of claim 1 where X is $SnBu_3$.

* * * * *

UNITED STATES PATENT AND TRADEMARK OFFICE
CERTIFICATE OF CORRECTION

PATENT NO. : 5,334,728
DATED : August 2, 1994
INVENTOR(S) : Kung et al.

It is certified that error appears in the above-indentified patent and that said Letters Patent is hereby corrected as shown below:

At Column 3, line 51, delete "67 1" and insert --- 671 --- therefor.

At Column 19, line 1, between "7.5(2H,s)," and 4.0(3H,s)," insert --- 7.1 (1H,s), ---

At Column 21, line 29, delete "rain" and insert --- min --- therefor.

Signed and Sealed this

Tenth Day of October, 1995

Attest:

BRUCE LEHMAN

*Attesting Officer*  *Commissioner of Patents and Trademarks*